United States Patent
Schmitt et al.

(10) Patent No.: US 12,203,813 B2
(45) Date of Patent: *Jan. 21, 2025

(54) TEMPERATURE DETERMINATION USING A CAMERA

(71) Applicant: Apple Inc., Cupertino, CA (US)

(72) Inventors: Joseph M. Schmitt, Cupertino, CA (US); Pablo A. Escobar, San Francisco, CA (US); Zijing Zeng, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/224,204

(22) Filed: Jul. 20, 2023

(65) Prior Publication Data
US 2024/0019317 A1 Jan. 18, 2024

Related U.S. Application Data

(60) Division of application No. 17/145,150, filed on Jan. 8, 2021, now Pat. No. 11,747,218, which is a
(Continued)

(51) Int. Cl.
*G01K 11/12* (2021.01)
*A61B 1/04* (2006.01)
(Continued)

(52) U.S. Cl.
CPC ............... *G01K 11/12* (2013.01); *A61B 1/042* (2013.01); *A61B 1/07* (2013.01); *A61B 1/227* (2013.01);
(Continued)

(58) Field of Classification Search
CPC .......... A61B 1/042; A61B 1/07; A61B 1/227; A61B 2560/0238; A61B 2562/0233; A61B 2562/0276; A61B 2562/164; A61B 5/0077; A61B 5/0082; A61B 5/015; A61B 5/6817; A61B 5/6898; A61B 5/7425; G01J 1/50;
(Continued)

(56) References Cited

U.S. PATENT DOCUMENTS 5,580,172 A 12/1996 Bhardwaj et al.
6,575,620 B1 6/2003 Banaszak et al.
(Continued)

*Primary Examiner* — Mohammed S Rahaman
(74) *Attorney, Agent, or Firm* — Brownstein Hyatt Farber Schreck, LLP

(57) ABSTRACT

A camera attachment for measuring a temperature of a surface, and related methods of measuring the temperature of the surface, employ a temperature reactive material that is thermally coupled with the surface and imaged to provide image data of the temperature reactive material that is analyzed to measure the temperature. A camera attachment for measuring a temperature of a surface includes a distal surface configured to be thermally coupled with the surface, a frame configured to be coupled with a camera that has a field of view, and a temperature reactive material coupled with the frame and thermally coupled with the distal surface. The frame positions the temperature reactive material within the field of view of the camera so that an image captured by the camera includes at least a portion of the temperature reactive material.

19 Claims, 16 Drawing Sheets

Related U.S. Application Data continuation of application No. 15/942,167, filed on Mar. 30, 2018, now Pat. No. 10,890,494.

(60) Provisional application No. 62/478,978, filed on Mar. 30, 2017.

(51) Int. Cl.
| | |
|---|---|
| *A61B 1/07* | (2006.01) |
| *A61B 1/227* | (2006.01) |
| *A61B 5/00* | (2006.01) |
| *A61B 5/01* | (2006.01) |
| *F21V 8/00* | (2006.01) |
| *G03B 17/56* | (2021.01) |
| *G06T 7/00* | (2017.01) |
| *G06T 7/90* | (2017.01) |
| *H04N 23/55* | (2023.01) |
| *H04N 23/667* | (2023.01) |
| *H04N 23/80* | (2023.01) |

(52) U.S. Cl.
CPC ............ *A61B 5/015* (2013.01); *A61B 5/6898* (2013.01); *G03B 17/565* (2013.01); *G06T 7/0004* (2013.01); *G06T 7/90* (2017.01); *H04N 23/55* (2023.01); *H04N 23/667* (2023.01); *H04N 23/80* (2023.01); *G02B 6/0001* (2013.01); *G06T 2207/10024* (2013.01)

(58) Field of Classification Search
CPC ...... G01K 11/12; G02B 6/0001; G03B 15/00; G03B 17/565; G06T 2207/10024; G06T 7/0004; G06T 7/90; H04N 23/10; H04N 23/50; H04N 23/55; H04N 23/667; H04N 23/80; H04N 5/33
See application file for complete search history.

(56) References Cited

U.S. PATENT DOCUMENTS

| | | |
|---|---|---|
| 6,648,506 B2 | 11/2003 | McGrath et al. |
| 7,069,169 B2 | 6/2006 | Nakakita et al. |
| 8,021,041 B2 | 9/2011 | Nakatani et al. |
| 8,734,009 B2 | 5/2014 | Toms et al. |
| 9,305,366 B2 | 4/2016 | Stark |
| 10,890,494 B1 | 1/2021 | Schmitt et al. |
| 2007/0071425 A1* | 3/2007 | Horinouchi .......... A63F 13/214 396/54 |
| 2011/0232330 A1 | 9/2011 | Noni, Jr. |
| 2012/0257882 A1 | 10/2012 | Kikuchi |
| 2013/0083823 A1* | 4/2013 | Harr .................... G01J 5/07 374/121 |
| 2013/0215928 A1 | 8/2013 | Bellifemine |
| 2013/0230074 A1 | 9/2013 | Shin |
| 2015/0133906 A1 | 5/2015 | Horton et al. |
| 2015/0374208 A1* | 12/2015 | Ruppersberg .......... A61B 1/227 600/109 |
| 2016/0134793 A1 | 5/2016 | Samanta |
| 2016/0316119 A1 | 10/2016 | Kent |
| 2017/0143198 A1* | 5/2017 | Xiao ...................... A61B 1/07 |
| 2017/0241843 A1 | 8/2017 | Jeon et al. |
| 2017/0299194 A1 | 10/2017 | Kamei et al. |
| 2018/0172521 A1 | 6/2018 | Diglio |
| 2019/0154513 A1 | 5/2019 | Frank |
| 2019/0270409 A1* | 9/2019 | Takashimizu ............. B60R 1/06 |
| 2021/0208010 A1 | 7/2021 | Schmitt et al. |

* cited by examiner

TEMPERATURE DETERMINATION USING A CAMERA

CROSS-REFERENCE TO RELATED APPLICATIONS

The present application is a division of U.S. patent application Ser. No. 17/145,150, filed Jan. 8, 2021, which is a continuation of U.S. patent application Ser. No. 15/942,167, filed Mar. 30, 2018, which claims the benefit of U.S. Provisional Application No. 62/478,978, filed Mar. 30, 2017, the entire contents of which are hereby incorporated by reference herein.

BACKGROUND

The present disclosure generally relates to temperature measurement systems and methods. In some embodiments, an image processing method is provided for measuring temperature. In further embodiments, a camera attachment is provided for measuring temperature.

There are different types of existing temperature measurement devices. For example, there are different types of existing thermometers used to measure body temperature. One such type of thermometer is a mercury thermometer. Other types of thermometers include infrared thermometers and thermistor thermometers. A liquid crystal thermometer can also be used to measure body temperature via skin contact. While such devices are generally acceptable for measuring temperature, it may be advantageous to increase the availability and accessibility of temperature measurements.

SUMMARY OF THE DISCLOSURE

The present disclosure generally relates to temperature measurement systems and methods. Some embodiments of the present disclosure increase the availability and accessibility of temperature measurements. For example, in some embodiments, an image processing method is provided for measuring temperature. In some embodiments, temperature measurement is based on image data and specifically based on image data associated with a temperature reactive material (TRM). Further, in some embodiments, a camera attachment is provided for measuring temperature. In some embodiments, the camera attachment is configured to couple with a smartphone. Given the ubiquitous nature of smartphones, the attachment can be used to convert a smartphone into a temperature measurement device to provide readily accessible temperature measurements. In some embodiments, the attachment is a passive attachment (without electronics or need for a power supply) and may thereby reduce manufacturing costs and increase availability.

For example, in some embodiments, a camera attachment is provided that includes a frame configured to couple with a camera. The camera has a field of view. In some embodiments, the camera attachment includes a temperature reactive material (TRM) that is coupled with the frame. The frame is configured to position the TRM within the field of view of the camera such that images captured by the camera include at least a portion of the TRM.

In some embodiments, the frame is configured to position the TRM directly within the field of view of the camera. For example, the frame can position the TRM directly within the field of view of the camera in embodiments without any intervening objects and/or optics between the TRM and the camera. As another example, the frame can position the TRM directly within the field of view of the camera in embodiments with one or more lenses disposed between the TRM and the camera. As yet another example, the frame can position the TRM directly within the field of view of the camera in embodiments in which one or more lenses are positioned between the TRM and the camera, and the one or lenses (e.g., a fish-eye lens) increase the field of view of the camera such that the TRM is positioned in the increased field of view but would be outside the regular field of view if the one or more lenses were not present.

In some embodiments, the frame positions the TRM indirectly within the field of view of the camera. For example, a mirror and/or one or more lenses can be coupled with the frame, and the frame can position the TRM indirectly within the field of view of the camera such that the TRM is imaged via the mirror and/or through the one or more lenses.

In some embodiments, the TRM includes a temperature reactive paint. Optionally, the TRM comprises a first temperature reactive film. In some embodiments, the TRM comprises the first temperature reactive film and a second temperature reactive film. The first temperature reactive film can be responsive to a first temperature range and the second temperature reactive film can be responsive to a second temperature range, which can be the same or different than the first temperature range. In still further embodiments, multiple discrete temperature reactive films are utilized, each of which can be particularly sensitive to certain temperature ranges and/or can overlap in temperature range.

In some embodiments, the camera attachment includes a contact plate that is thermally coupled with a distal side of the TRM. The distal side of the TRM can be opposite a proximal side of the TRM that is imaged by the camera.

In some embodiments, the camera attachment includes one or more springs (e.g., a compression spring(s)) that bias a position of the contact plate relative to the frame. In such embodiments, the one or more springs accommodates movement of the contact plate relative to the frame to inhibit or prevent high contact pressure, which can alter the temperature of a skin surface region via induced alteration of blood flow.

In some embodiments of the camera attachment, the TRM is thermally insulated from the frame. For example, the TRM can be thermally insulated from the frame via a thermal insulation such as a foam, an air gap, and/or the like.

Optionally, the camera attachment can include a light pipe that is configured to optically couple with a light source (e.g., a flash unit) of the camera. The light pipe can deliver light energy from the light source of the camera toward the TRM to illuminate the TRM.

The camera attachment can be passive or active. For example, the camera attachment can be passive (e.g., lacking a power source or electronics). In other embodiments, the temperature monitoring portion is passive and the attachment is powered to provide additional functionality (e.g., the frame can be part of a phone case supporting an external power source for charging the phone and/or a powered sensor).

In some embodiments, a method of measuring a temperature is provided. The method includes receiving camera image data. The camera image data includes image data associated with a TRM. The method further include analyzing the image data associated with the TRM to measure a temperature of the TRM. Thereafter, the measured temperature can be processed in any suitable fashion including, but not limited to, stored in memory, transferred to another application, and/or outputted to a user.

In some embodiments, the method includes switching the camera from a camera mode to a temperature analysis mode prior to analyzing the image data of the TRM. The temperature analysis mode can be configured to analyze the image data of the TRM by analyzing at least a portion of the image data associated with the TRM. In some embodiments, the camera can be switched from the temperature analysis mode to the camera mode. In the camera mode, the received image data can be processed to remove image data associated with the TRM from the received image data.

In some embodiments, the image data of the TRM is analyzed by assigning one or more color model values to the image data of the TRM, which in turn can be used to estimate a temperature of the TRM. The one or more color model values may, for example, be red-green-blue ("RGB") color model values, cyan-magenta-yellow-black ("CMYK") color model values, hue-saturation-brightness ("HSB") color model values, hue-saturation-lightness ("HSL") color model values, or YUV color model values (where the color space is defined in terms of one luma and two chrominance components), etc. Optionally, the image data associated with the TRM can be further analyzed to measure the temperature of the TRM by applying an equation to the one or more color model values that maps the one or more color model values to a temperature value. In some embodiments, the image data associated with the TRM is analyzed by accessing a lookup table that associates the one or more color model values to temperature values. In some embodiments, the lookup table is a two- or three-dimensional lookup table that provides accurate mapping between temperature and color model values.

This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The disclosure will be better understood on reading the following description and examining the figures that accompany it. These figures are provided by way of illustration only and are in no way limiting on the disclosure.

BRIEF DESCRIPTION OF THE DRAWINGS

Further details, aspects and embodiments of the disclosure will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE DISCLOSURE

The present disclosure generally relates to temperature measurement systems and methods. In some embodiments, a camera attachment is provided that enables image based temperature measurement and is low cost. In some embodiments, the attachment is configured to be coupled with a smartphone to take advantage of the integrated camera and processing power to measure the temperature of an object. Accordingly, in some embodiments, the camera attachment and image processing methods can be used to take body temperature measurements. In many embodiments, these systems and methods utilize color changes in a temperature reactive material (TRM) to measure the temperature of an object.

Figure 1:
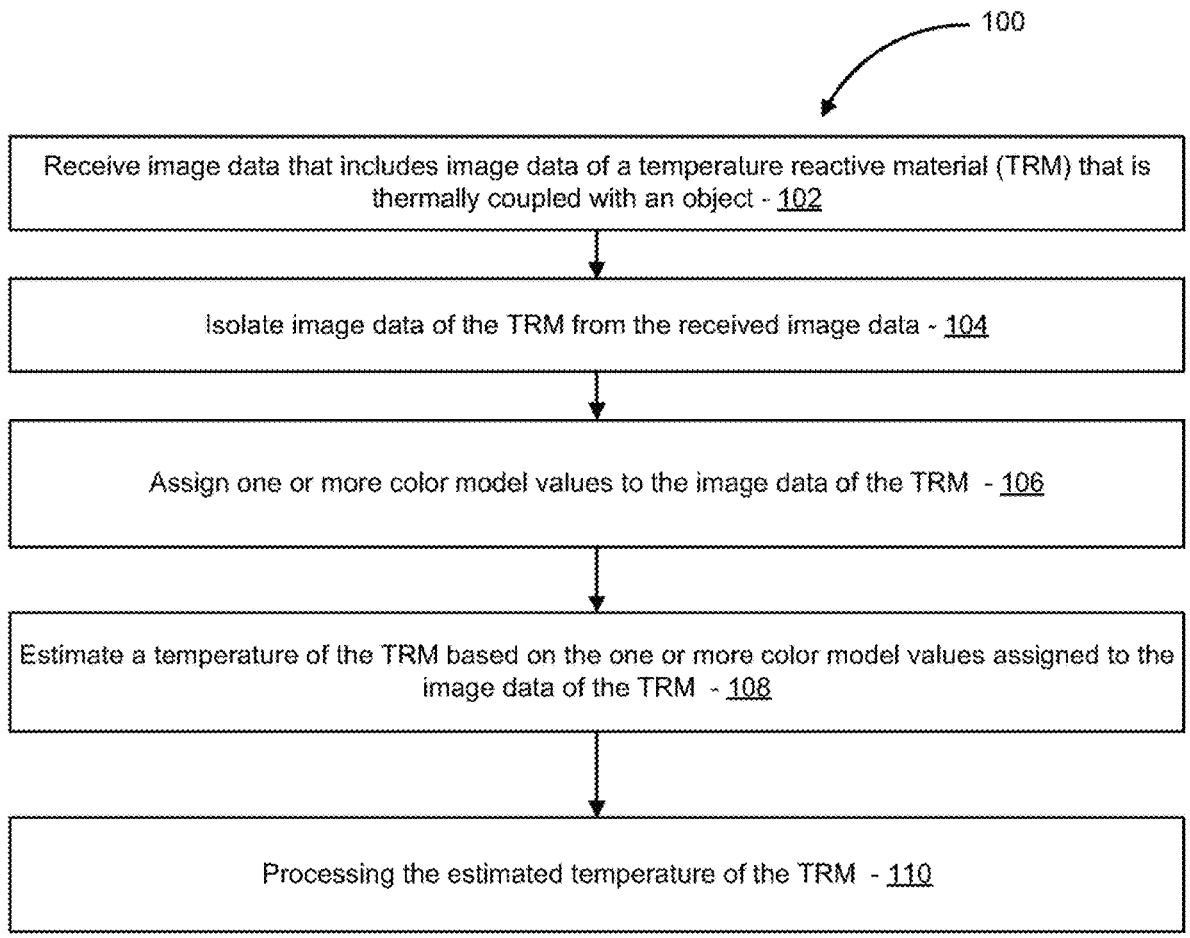
FIG. 1 illustrates an exemplary method of measuring temperature according to some embodiments of the disclosure.

FIG. 1 illustrates an exemplary method 100 of measuring temperature according to some embodiments of the disclosure. Any suitable device, including the camera attachments described herein, can be used to practice the method 100. Method 100 includes receiving image data that includes image data associated with a TRM that is thermally coupled with an object (act 102). Data associated with at least a portion of the TRM can be isolated from the received image data (act 104). One or more color model values is assigned to image data associated with the TRM (act 106). A temperature of the TRM is estimated based on the one or more color model values assigned to the image data associated with the TRM (act 108). Thereafter, the estimated temperature of the TRM can be processed in any suitable manner (act 110). For example, the estimated temperature can be stored in memory and/or sent to another application for use. The estimated temperature can be output to the user at any suitable time and/or in any suitable manner.

Figure 2:
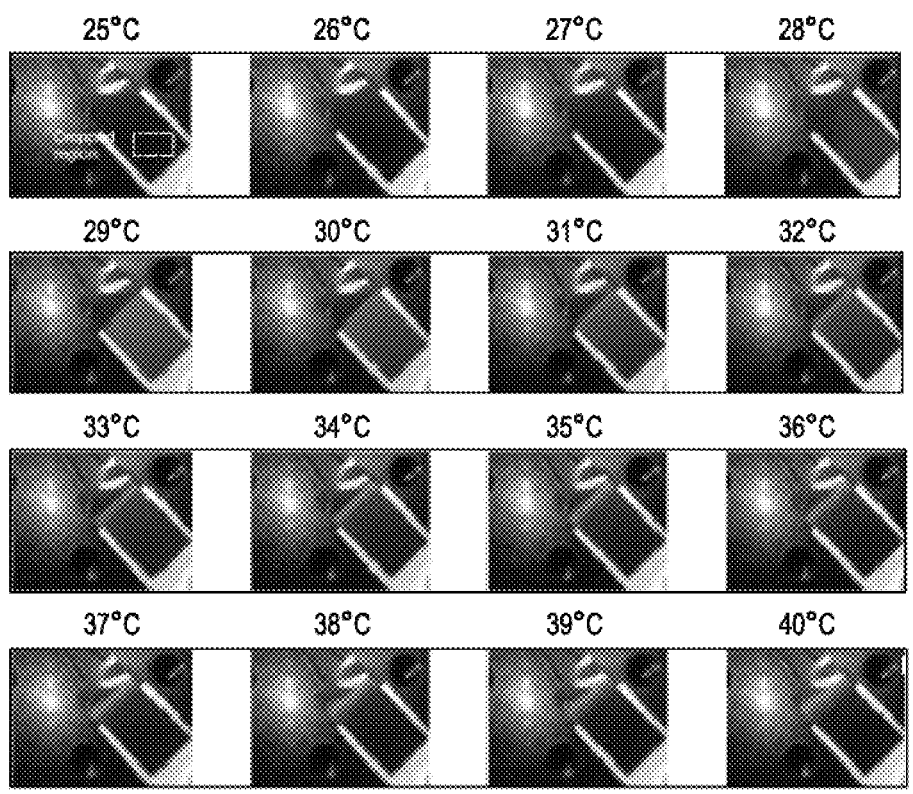
FIG. 2 shows a plurality of images of a temperature reactive material (TRM) captured by a camera.

As mentioned above, the image processing methods disclosed herein may take advantage of color changes in a TRM in order to measure the temperature of an object that is thermally coupled with the TRM. Accordingly, in many embodiments, the image data processed includes image data associated with a TRM. For example, FIG. 2 illustrates a plurality of images 200 of a TRM captured by a camera at different temperatures ranging from 25° C. in the top left image and incrementally increasing by 1° C. to 40° C. in the bottom right image. The imaged TRM comprises a thermochromic liquid crystal film (LC-3035, Educational Innovations, Inc.) and the temperature of the liquid crystal film was controlled by a thermoelectric cooler. While the plurality of images 200 of the TRM include the entire sheet of the TRM, it should be understood that in some embodiments, only a portion of the TRM is captured in the image data that is processed to determine the temperature of the TRM.

As can be seen in the plurality of images 200 in FIG. 2, in some embodiments, the received image data includes image data in addition to the image data associated with the TRM. Accordingly, in some embodiments, image data associated with the TRM can be isolated from the received image data 104 and analyzed to measure temperature. For example, the top left image of the plurality of images 200 in FIG. 2 illustrates an exemplary isolated region 202, where image data associated with the TRM is isolated from the received image data 104. In some embodiments, the region 202 can be a user specified region. Alternatively, the region 202 can be a predetermined region of the received image data when the received image data is captured with a camera attachment that positions the TRM in a known location in the camera's field of view.

Figure 3:
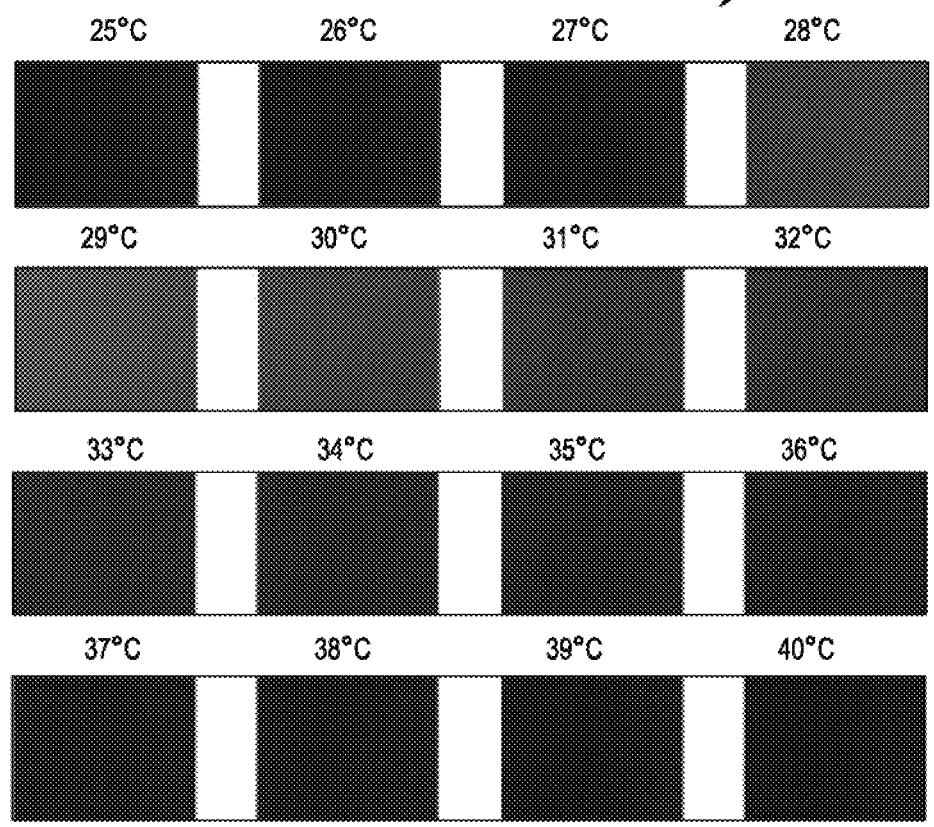
FIG. 3 shows isolated images of the TRM imaged by the camera in FIG. 2.

FIG. 3 illustrates isolated images 300 of the TRM photographed in FIG. 2. In some embodiments, the region 202 includes only a portion of the TRM, as can be seen in the color versions of FIG. 2 and FIG. 3, but in other embodiments, the region 202 includes all of the TRM.

Once the image data associated with the TRM is isolated or otherwise localized from the received image data, one or more color model values can be assigned to the image data associated with the TRM (act 106). In some embodiments, the one or more color model values are assigned based on the average color model values for the isolated region of the image data. The one or more color model values may, for example, be red-green-blue ("RGB") color model values, cyan-magenta-yellow-black ("CMYK") color model values, hue-saturation-brightness ("HSB") color model values, hue-saturation-lightness ("HSL") color model values, or YUV color model values (where the color space is defined in terms of one luma and two chrominance components), etc.

Figure 4:
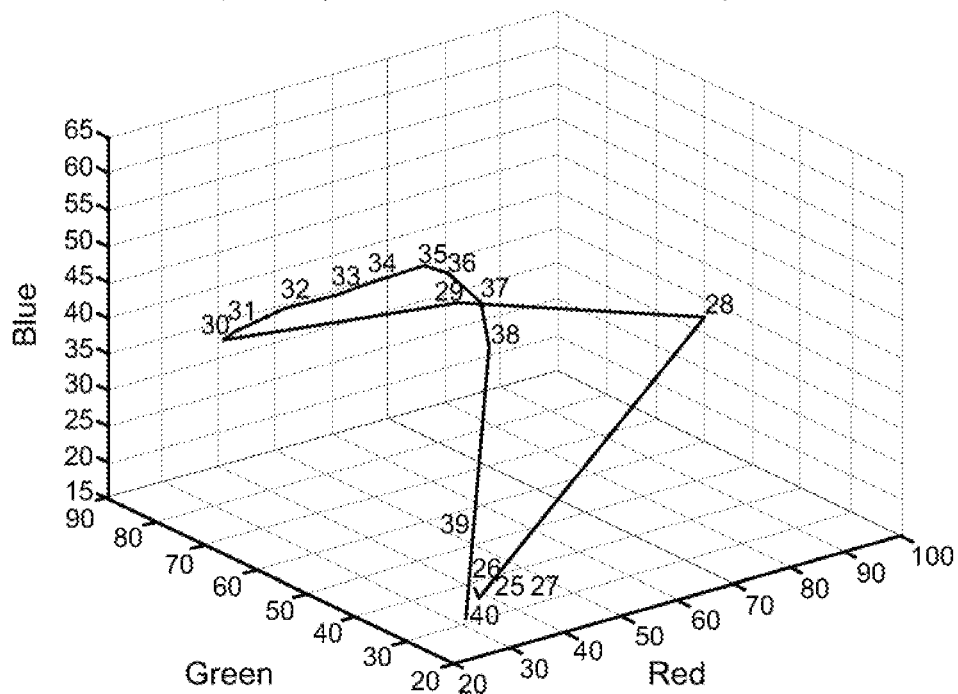
FIG. 4 illustrates an exemplary three-coordinate lookup table associating RGB values with temperature.

For example, FIG. 4 shows the temperatures of the temperature reactive film imaged and isolated in FIG. 2 and FIG. 3, respectively, in RGB coordinate space. As can be seen in FIG. 4, for the particular TRM imaged and isolated in FIG. 2 and FIG. 3, when heating the TRM from 25° C. to 28° C., the red value increases significantly, with moderate increases in green and blue values. Continued heating of the TRM from 28° C. to 30° C. resulted in a decrease in red and blue values, with a continued increase in green value. Further heating of the TRM from 30° C. to 36° C. resulted in an increase in blue value and decreases in red and green values. Heating of the TRM from 36° C. to 40° C. resulted in decreases in red, green, and blue values. The above-described temperature/color profile for the particular TRM imaged and isolated in FIG. 2 and FIG. 3 is for one exemplary material and other materials may have a different temperature/color profile(s).

Figure 5:
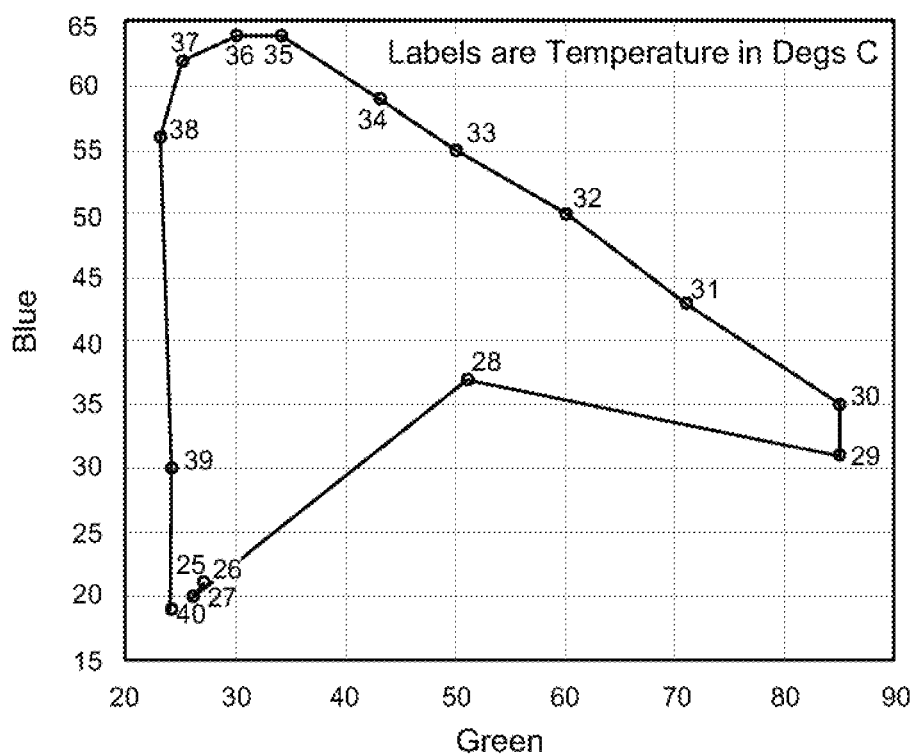
FIG. 5 illustrates an exemplary two-coordinate lookup table associating blue and green values with temperature.

Thereafter, a temperature of the TRM can be determined based on the one or more color model values assigned to the image data associated with the TRM (act 108). The temperature can be calculated based on a calibration equation or by accessing a look-up table that associates the one or more color model values to temperature. For example, based on the temperature of the temperature reactive film in RGB coordinate space shown in FIG. 4, an exemplary two-coordinate lookup table was generated associating blue and green values with temperature, as can be seen in FIG. 5. After calculating the temperature, the resulting temperature value can be processed in any suitable manner (act 110) (e.g., stored in memory, output to another application, and/or outputted to a user).

As mentioned above, in some embodiments, the image data associated with the TRM is captured with the assistance of a camera attachment. In many embodiments, the camera attachment includes the TRM and positions the TRM within a field of view of the camera. The camera attachment can be configured to be attached to any suitable device that includes a camera.

For example, in some embodiments, the camera attachment is configured to be attached to a mobile phone that includes a camera. In such embodiments, the camera attachment can include a frame/adapter that forms an aperture that receives and accommodates a portion of the mobile phone. In some embodiments, the frame/adapter limits the extent to which the mobile phone can be inserted into the aperture so as to position the TRM within the field of view of the camera when the camera is fully inserted into the aperture. In some embodiments, the camera attachment includes a frame/adapter that also functions as a case for the mobile phone. In some embodiments, the camera attachment includes a frame/adapter that is configured to be clipped onto a portion of the phone, and, in some embodiments, may need to be manually positioned relative to the phone (e.g., by a user of the phone) to position the TRM within the field of view of the camera. In such embodiments, the phone can be configured to provide feedback that aids in the manual positioning of the frame/adapter relative to the camera. For example, the camera can capture one or more images that can be analyzed (e.g., by the user, automatically via image processing software executed by the phone) to determine: (a) if the TRM is suitably positioned within the field of view of the camera and/or (b) if the frame/adapter needs to be repositioned relative to the camera to suitably position the TRM within the field of view of the camera and, if so, in what direction and by what amount. In such embodiments, the frame/adapter can include one or more features (e.g., one or more fiducial markers) that can be identified in the one or more images and the position of the one or more features in the image used to generate the feedback provided to aid in the positioning of the frame/adapter relative to the camera.

As another example, in some embodiments, the camera attachment is configured to be attached to a dedicated camera device (e.g., a single lens reflex (SLR) camera, a point-and-shoot camera). In some embodiments, the camera attachment can include a frame/adapter that forms an aperture configured to receive and accommodate a portion of the camera's lens barrel so as to position the TRM in the field of view when the lens barrel is positioned in the aperture. In some embodiments, the camera includes image processing software that automatically analyzes one or more particular predetermined portions of a captured image that include the TRM to make a temperature measurement. This may be advantageous, especially when the camera attachment has other functions, embodiments of which are described in further detail below. Further, a portion of the camera attachment can serve as a color reference that can be used to calibrate color values of the TRM. For example, the color reference can have known color values (gray, white, blue, green, yellow, or red color reference, or the like) so that color values of the TRM can be calibrated between multiple images. In some embodiments, the camera attachment includes one or more fiducial markers that indicate where the color reference is located. In some embodiments, the camera attachment includes a readable label (e.g., a barcode label) that identifies a type/model of the camera attachment. In such embodiments, the type/model of the camera attachment can then be used to identify where the color reference and/or the TRM is located. In some embodiments, the camera attachment positions the color reference within the field of view of the camera, similar to the TRM. Moreover, in some embodiments, the color reference is positioned in a predetermined location within the camera's field of view so that corresponding image processing software can automatically analyze a particular predetermined location of the captured images to analyze the color reference and to thereafter calibrate color values of the TRM accordingly.

Figure 6:
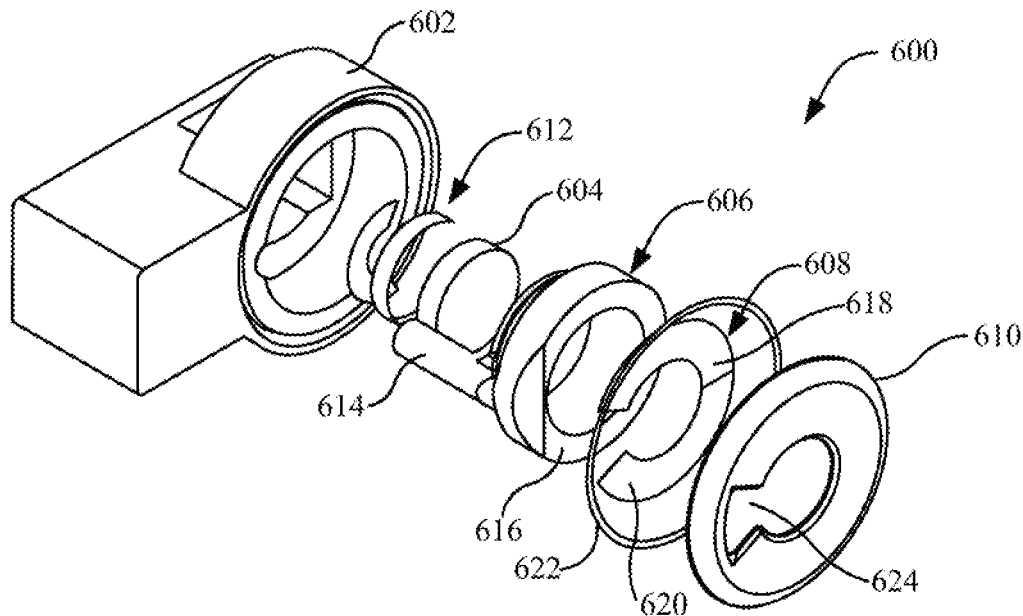
FIG. 6 illustrates an exploded view of an exemplary camera attachment for temperature measurement according to some embodiments.

FIG. 6 illustrates an exploded view of an exemplary camera attachment 600 for temperature measurement according to some embodiments. Furthermore, in some embodiments, camera attachment 600 can be used to provide dermatoscope functionality to an attached camera. In the illustrated embodiment, camera attachment 600 is configured to be attached to a smartphone to cooperate with a camera and a light source of the smartphone.

Camera attachment 600 includes a frame 602, a TRM 608, and a contact member 610. In the illustrated embodiment, the camera attachment further includes an optional lens 604 and an optional light pipe 606, which can be omitted in some embodiments. In some embodiments, frame 602 includes an opening for allowing the camera of the smartphone to capture images therethrough. In some embodiments, frame 602 is configured to position each of the components 604, 606, and 608 in a known relationship with a camera of the smartphone. Frame 602 can align the optical axis of the lens 604 with an optical axis of the camera of the smartphone. Additionally, the frame 602 can position the light pipe 606 relative to the smartphone such that a proximal end of the light pipe 606 is optically coupled with a light source of the smartphone. Moreover, the frame 602 can position at least a portion of the TRM 608 within a field of view of the smartphone camera when the frame 602 is coupled thereto. In some embodiments, the frame 602 is configured for attachment to the phone (e.g., via an opening in the frame 602 into which a portion of the phone is inserted). In other embodiments, the frame 602 is configured for attachment to an adapter (e.g., adapter 702 described below) that is configured for attachment to the phone.

In some embodiments, lens 604 provides additional magnification to the camera of an attached smartphone. The additional magnification may be useful when the smartphone is used as a dermatoscope. The lens 604 can be coupled to the frame 602 using any suitable approach, for example, via a suitable adhesive, and/or via a suitable non-adhesive mechanism (e.g., mechanical attachment). In some embodiments, the lens 604 is positioned about the opening of frame 602 such that frame 602 aligns the optical axis of the lens 604 with the camera of the smartphone when the attachment 600 is coupled thereto.

Light pipe 606 can include a proximal portion 614 and a distal portion 616. The proximal portion 614 of light pipe 606 can be configured to optically couple with the light source of the smartphone. Light pipe 606 can direct and/or diffuse light from the light source of the smartphone from the proximal portion 614 toward the distal portion 616 to illuminate the camera's field of view when capturing images. In some embodiments, the distal portion 616 comprises a ring with an aperture. An axis of the aperture can be aligned with an axis of the lens 604. In some embodiments, light pipe 606 is not included. For example, some embodiments of the attachment 600 can include a separate light source or ambient light for illuminating the TRM 608.

In many embodiments, the TRM 608 includes any suitable material that has an optical characteristic, such as color, that changes responsive to temperature of the TRM 608 over a predetermined temperature band. The TRM 608 can have any suitable configuration. For example, in some embodiments, the TRM 608 comprises a laminated or painted thermochromic film. In the illustrated embodiment, TRM 608 comprises a first thermochromic film 618 and a second thermochromic film 620. In the illustrated embodiment, the films 618, 620 are arcuate strips positioned around the opening of the frame 602. The first and second thermochromic films 618, 620 can be designed for increased sensitivity to a particular temperature range. For example, the first thermochromic film 618 can be a 30-35° C. range liquid crystal sheet and second thermochromic film 620 can be a 35-40° C. range liquid crystal sheet. While illustrated as including two films, it should be understood that other embodiments can utilize a single sheet of a TRM, as illustrated in the example of FIGS. 2-5. In other embodiments, a plurality of separate films can be used (e.g., 2, 3, 4 or more) to increase temperature measurement resolution. Additionally, the TRM sheets can be reactive to different temperature ranges, larger temperature ranges (e.g., greater than 5° C. range), and/or smaller temperature ranges (e.g., less than 5° C. range) and can also be reactive to temperature ranges that overlap. In some embodiments, it may be beneficial to utilize TRM where color change is linear over the assigned temperature measurement range, however TRMs with non-linear color changes are also possible for use in the attachment.

Contact member 610 can have any suitable configuration. For example in the illustrated embodiment, contact member 610 has a ring configuration. In some embodiments, the contact member 610 is configured to conduct heat from the surface contacted by the contact member 610 to the TRM 608. In many embodiments, some or all of the contact member 610 is formed of a heat-conductive material (e.g., aluminum, brass, stainless steel, copper, metal alloys, etc.). In some embodiments, the heat-conductive portion of the contact member 610 is thermally coupled with a distal side of the TRM 608 that is opposite of a proximal side of the TRM 608 that is imaged by the camera when the attachment 600 is in use. In some embodiments, the TRM 608 is adhered to the contact member 610 with an adhesive. In some embodiments, the adhesive comprises a thermal paste, which can also help to transfer heat between the contact member 610 and the TRM 608. Optionally, the contact member 610 supports the TRM 608 relative to the frame 602 and helps thermally isolate the TRM 608 from the remainder of attachment 600. In some embodiments, the contact member 610 couples to the frame 602 along an outer perimeter of contact member 610 by a pressure reactive adhesive 622 with high thermal conductivity. In some embodiments, a spring can be used to bias the position of the contact member 610 relative to the frame 602 so as to limit contact pressure between the contact member 610 and a surface contacted by the contact member 610.

Additionally, in the illustrated embodiment, contact member 610 includes an aperture 624 shaped to enable the camera to capture an image that includes something in front of the aperture 624. In the illustrated embodiment, the aperture 624 has a portion sized and located to allow light conducted through the light pipe 606 to be emitted from the distal portion 616 of light pipe 606 to illuminate the area in front of contact member 610. This may be advantageous when the smartphone is used to capture images as a dermatoscope. To limit reflections of the light off of the contact member 610 when in an image capture mode, the proximal surface of the contact member 610 can be roughened and/or can include an anti-reflective coating or dark/blackened surface. While contact member 610 has a ring configuration in the illustrated embodiment, the contact member 610 can have any other suitable configuration (e.g., partial annulus or the like).

Figure 7:
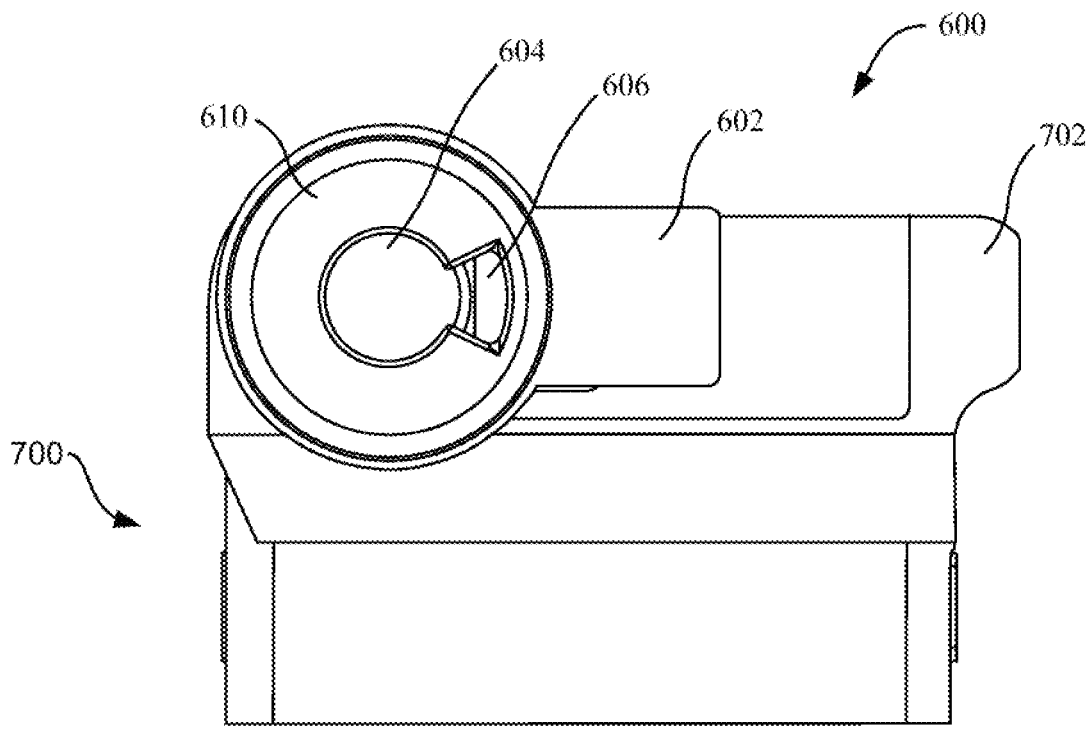
FIG. 7 illustrates the attachment of the exemplary camera attachment of FIG. 6 to a smartphone according to some embodiments.

FIG. 7 illustrates the distal side of the exemplary camera attachment 600 of FIG. 6 attached to a smartphone 700 that includes a camera, according to some embodiments. In the illustrated embodiment, camera attachment 600 is configured to couple to the smartphone 700 via an adaptor 702. In some embodiments, adaptor 702 is configured to be fitted over an end of smartphone 700 that includes the camera. Adaptor 702 can be configured to fit a number of different camera attachments, such as attachment 600. Accordingly, in some embodiments, adaptor 702 can remain fitted on smartphone 700, while various attachments (e.g., attachment 600) are interchanged on and off the smartphone 700. In some embodiments, adaptor 702 can slidably couple with attachment 600 such that the attachment 600 can be slid into position with the camera when the functionality of attachment 600 is desired (e.g., temperature measurement, dermatoscope) and slid out of position with the camera when the functionality of attachment 600 is not needed. While attachment 600 is illustrated with use of adaptor 702 to attach to smartphone 700, it should be understood that other attachment methods are possible. For example, attachment 600 may be integrated with adaptor 702 to attach directly to smartphone 700.

Figure 8:
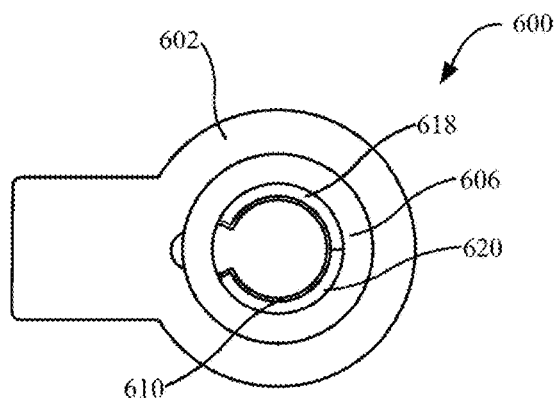
FIG. 8 illustrates the camera view of the smartphone camera through the exemplary camera attachment of FIG. 6.

FIG. 8 illustrates the proximal side of camera attachment 600 of FIG. 6 to illustrate a camera's field of view through the attachment 600. Images captured by a smartphone camera can include a portion/region of the image that is imaged through the opening of attachment 602 (e.g., when used as a dermatoscope, or the like) and a peripheral image of at least a portion of the first thermochromic film 618 and at least a portion of the second thermochromic film 620. When the portion/region of the image captured through the opening of the attachment 602 is of interest, software installed on the smartphone can provide a camera mode that is configured to remove the peripheral image of the first thermochromic film 618 and the second thermochromic film 620 so that only the portion/region of the image that is imaged through the opening of attachment 602 is outputted to the user. Additionally, in some embodiments, a contact member cover can be provided that is configured to be disposed over the contact member 610 when the smartphone is in camera mode. As mentioned above, contact member 610 may cause unintended light reflections in the central image. Accordingly, a contact member cover can be removably attached to the contact member 610 to reduce the light reflections caused by contact member 610. In some embodiments, the software installed on the smartphone is configured to detect when the contact member cover is attached (e.g., via detecting the presence of the contact member cover via image processing) and automatically switch to camera mode if not already in camera mode.

When temperature measurement is desired, software installed on the smartphone can switch to a temperature analysis mode that is configured to analyze captured image data to measure a temperature based on the image data associated with the peripheral image of the first thermochromic film 618 and the second thermochromic film 620. In some embodiments, when in temperature analysis mode, an image of the TRM 608 is not sent to the user and only the temperature measurement is delivered. Additionally, when a contact member cover is used, it can be removed from the contact member 610 to allow the contact member to directly contact a surface where a temperature reading is desired. Additionally, in some embodiments of the temperature analysis mode, when the portion/region of the image captured through the opening of the attachment 602 is also of interest, the camera software can be configured to display the portion/region of the image captured through the opening of the attachment 602 while simultaneously measuring (and optionally displaying) the measured temperature value.

Figures 9, 10:
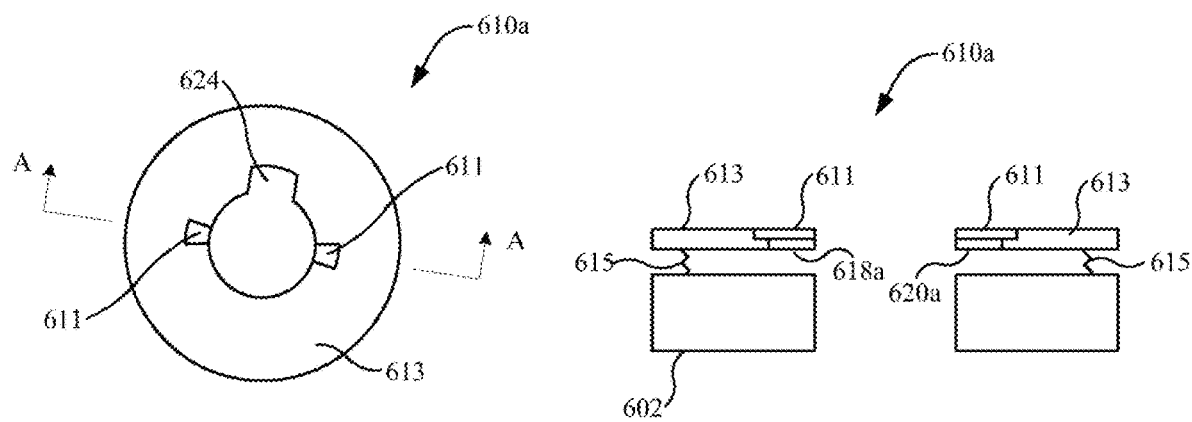
FIG. 9 illustrates a contact assembly for a camera attachment according to some embodiments.
FIG. 10 illustrates a cross-sectional view of the contact assembly of FIG. 9 along A-A.

FIG. 9 illustrates another contact member 610a for a camera attachment (e.g., attachment 600), according to some embodiments. FIG. 10 illustrates a cross-sectional view of contact member 610a along A-A of FIG. 9. Contact member 610a comprises thermally conductive elements 611 supported by a support member 613. Similar to contact member 610, contact member 610a includes an aperture 624 in the support member 613 to allow a light source of the smartphone to illuminate the area distal to the contact member 610a. As illustrated in FIG. 10, the TRM 618a, 620a can be adhered to or painted on the proximal side of conductive elements 611.

In the illustrated embodiment, the relatively small size of thermally conductive elements 611 provides low thermal mass to reduce the amount of time to achieve thermal equilibrium between the elements 611 and the object contacted by the elements 611 as compared to larger thermal mass conductive elements. In some embodiments, a thickness of each of the thermally conductive elements 611 is 500 µm or less (e.g., 100 µm). Additionally, it may be beneficial to thermally isolate each of the thermally conductive elements 611 from the support member 613 and the rest of the attachment. For example, in some embodiments, the support member 613 comprise a material that is less thermally conductive than the elements 611. Additionally, a layer of foam material can be disposed between each of the thermally conductive elements 611 and the support member 613 to help thermally isolate the thermally conductive element 611 and the TRM from the rest of the attachment. Further, in some embodiments, one or more springs 615 (e.g., a compression spring or the like) can be used to bias the position of the contact member 610a relative to the frame 602. In such embodiments, the one or more springs 615 can be configured to accommodate proximal movement of the contact member 610a relative to the frame 602 to reduce contact pressure between the contact member 610a and the object contacted by the contact member 610a. In the alternative, springs 615 can be replaced by rigid posts.

Figure 11:
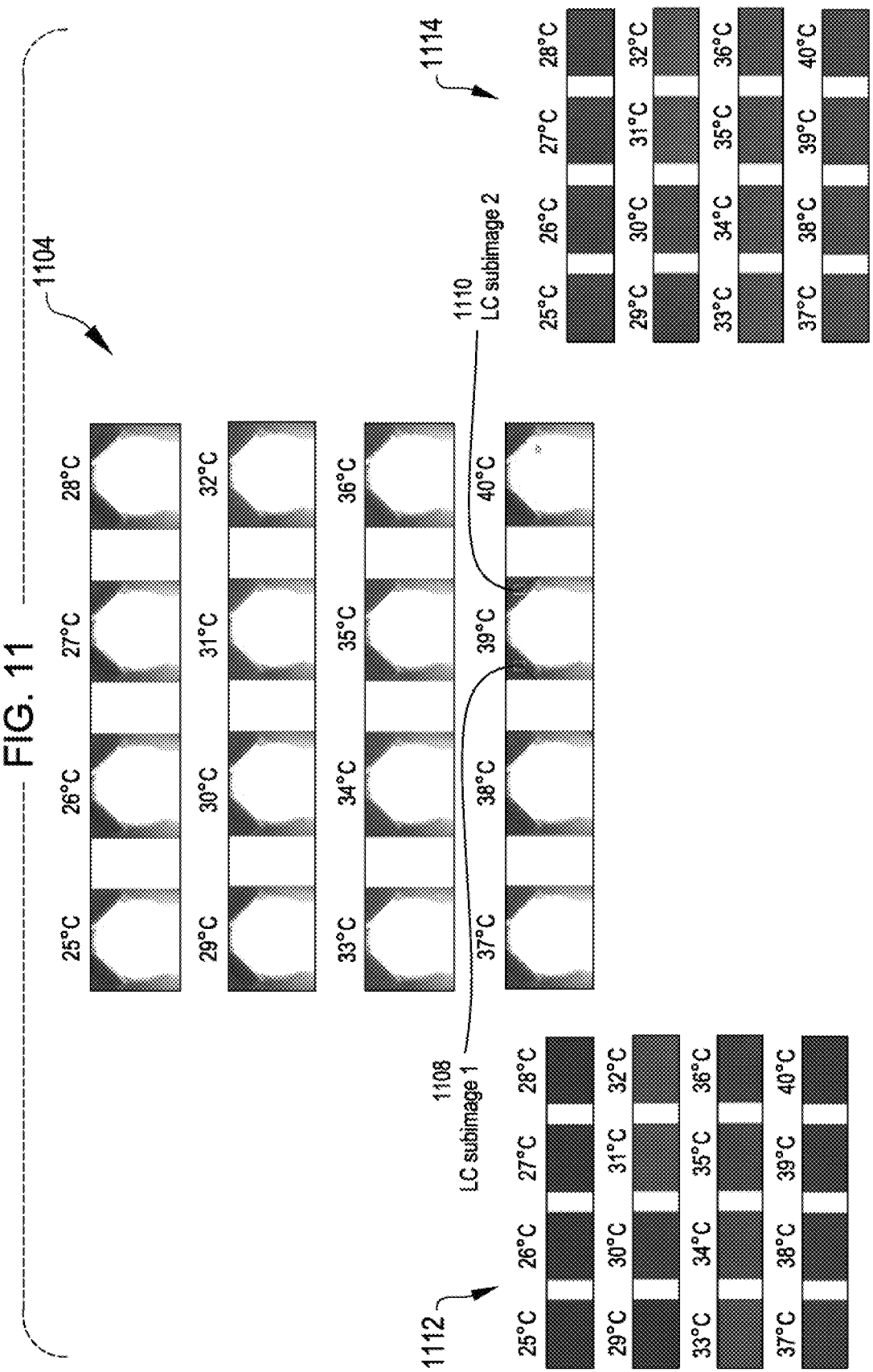
FIG. 11 shows a set of images captured with a camera with a contact assembly similar to that illustrated in FIG. 9.

FIG. 11 illustrates a set of images captured with a camera with a contact member similar to that illustrated in FIG. 9. In the experimental setup, the contact member comprised a plastic cap with a white reflector in the image field. Additionally, the contact member comprised two strips of TRM. FIG. 11 illustrates a plurality of images 1104 of the TRM of the contact member captured by a camera at different temperatures of the TRM ranging from 25° C. in the top left image and incrementally increasing by 1° C. to 40° C. in the bottom right image. The temperature of the liquid crystal film TRM was controlled by a thermoelectric cooler. As can be seen in the captured images 1104, only a portion of each of the TRM strips is captured in the image data.

Image data associated with the TRM strips was isolated from the received image data 1104 during image processing for temperature measurement. For example, image 1106 of the plurality of images 1104 in FIG. 11 illustrates exemplary isolated regions 1108, 1110, each associated with one of the TRM strips, where image data associated with the TRM strips was isolated from the image data 1104. The regions 1108, 1110 can be user specified before or during image processing. Alternatively, the isolated regions 1108, 1110 can be predetermined locations in the received image data 1104 when the received image data is captured with the camera attachment that positions the TRM in a known location in the camera's field of view.

Figure 12:
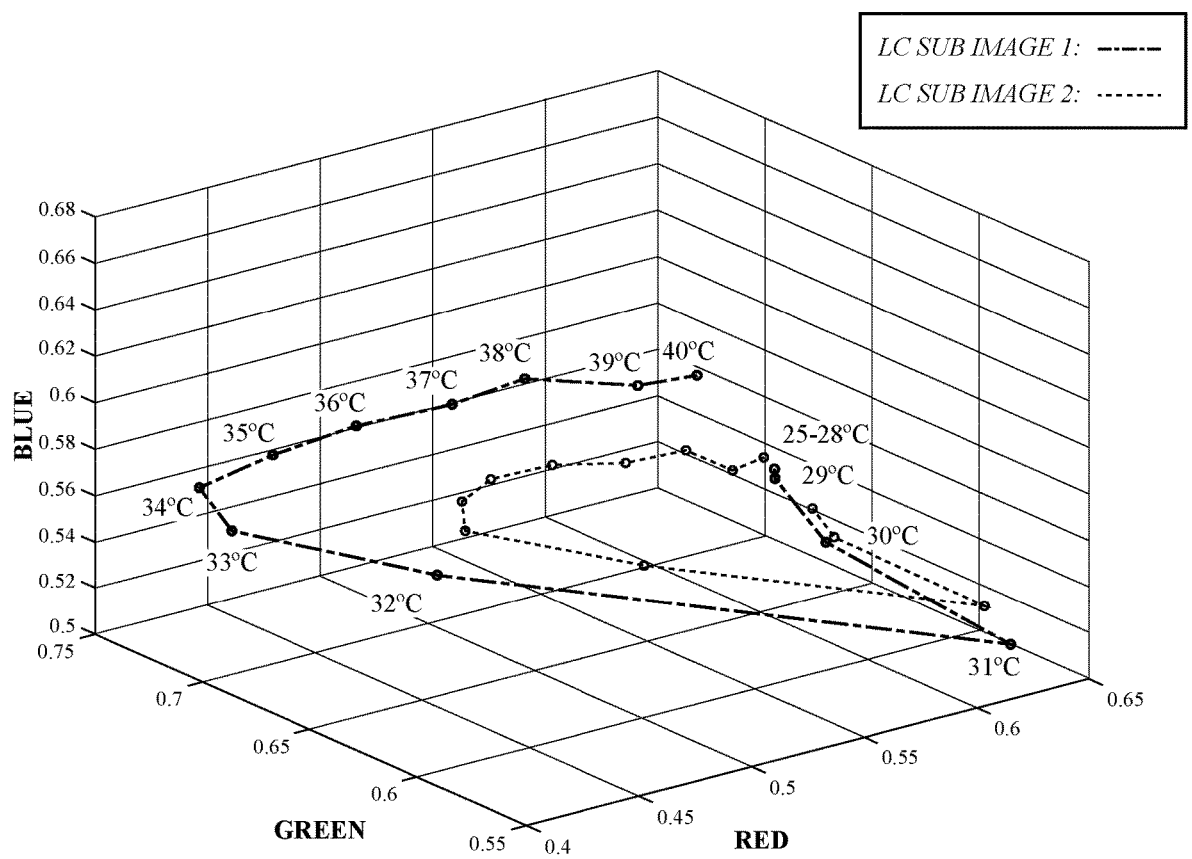
FIG. 12 illustrates an exemplary plot associating RGB values with temperature generated from the set of images illustrated in FIG. 11.

Isolated images 1112, 1114 of the TRM strips are illustrated at the bottom of FIG. 11. In some embodiments, the isolated regions 1108, 1110 include only a portion of the TRM, but in other embodiments, the isolated regions 1108, 1110 include all of the TRM strips. FIG. 12 illustrates an exemplary plot associating RGB values with temperatures generated from the set of images illustrated in FIG. 11. The blue line associates RGB values from the isolated regions 1112 with temperature and the green line associates the RGB values from the isolated regions 1114 with temperature. In the plot, the average RGB values in subimage regions are normalized to average intensity in the regions using the following:

$$R_n = \frac{R}{\text{sqrt}(R^2 + G^2 + B^2)}$$

$$G_n = \frac{G}{\text{sqrt}(R^2 + G^2 + B^2)}$$

$$B_n = \frac{B}{\text{sqrt}(R^2 + G^2 + B^2)}$$

From the images of FIG. 11 and their corresponding plots in FIG. 12, white haze may reduce the span of color change of the TRM strips. Additionally, the Red-Green projection may contain the most temperature information.

Figure 13:
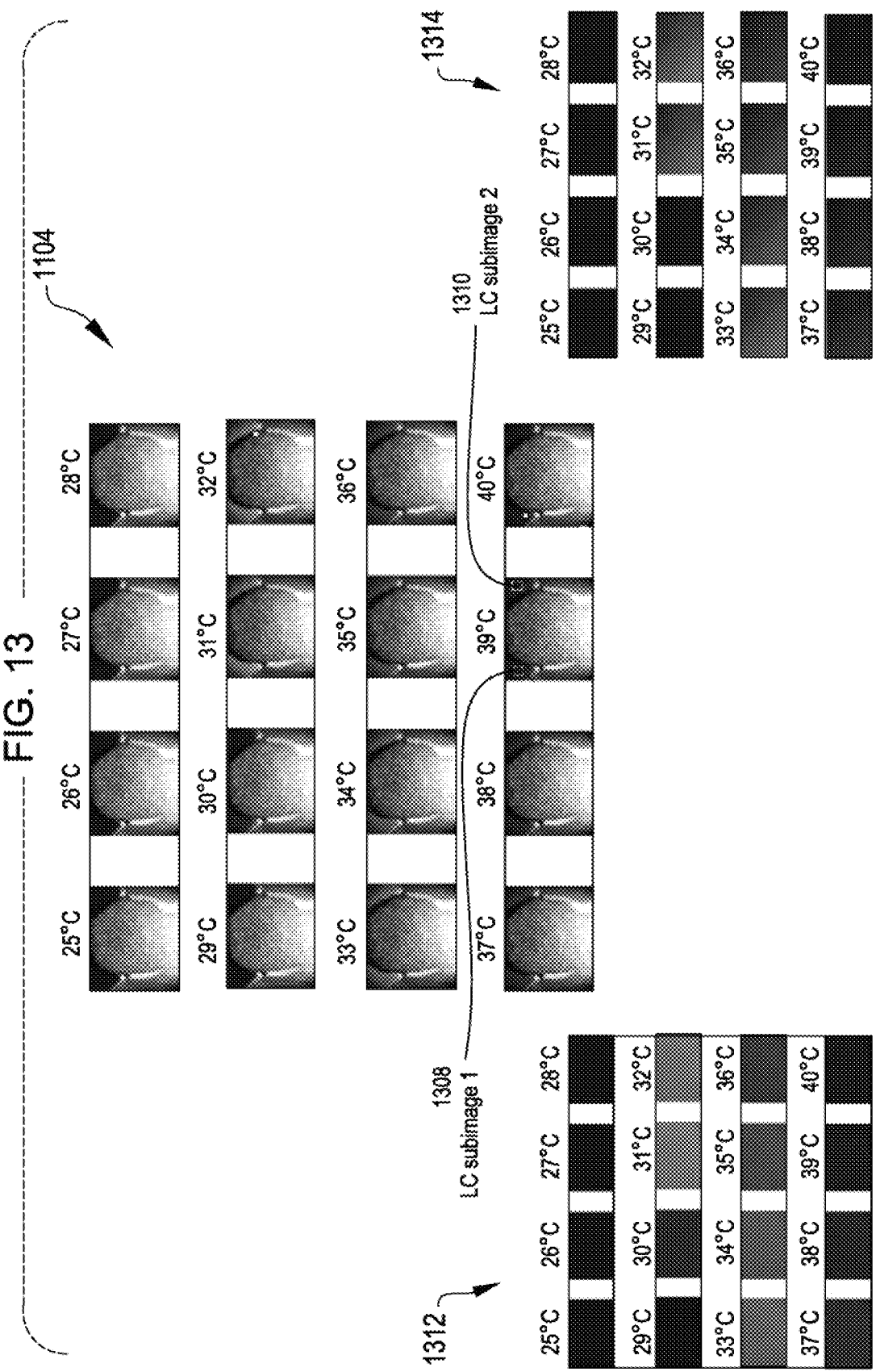
FIG. 13 shows another set of images captured with a camera with a contact assembly similar to that illustrated in FIG. 9.

FIG. 13 illustrates another set of images captured with a camera with a contact member similar to that illustrated in FIG. 9. In the experimental setup, the contact member comprised a plastic cap with a black reflector in the image field. Additionally, the contact member comprised two strips of TRM, similar to the contact member illustrated used in the experiment of FIG. 11. FIG. 13 illustrates a plurality of images 1304 of the TRM strips captured by a camera at different temperatures of the TRM strips ranging from 25° C. in the top left image and incrementally increasing by 1° C. to 40° C. in the bottom right image. The temperature of the TRM strips was controlled by a thermoelectric cooler. As can be seen in the captured images 1304, only a portion of each of the TRM strips is captured in the image data.

Additionally, image data associated with the TRM strips was isolated from the received image data 1304 during image processing for temperature measurement. For example, image 1306 of the plurality of images 1304 in FIG. 13 illustrates exemplary isolated regions 1308, 1310, each associated with one of the TRM strips, where image data associated with the TRM strips was isolated from the image data 1304. The regions 1308, 1310 can be user specified before and/or during image processing. Alternatively, the isolated regions 1308, 1310 can be predetermined locations in the received image data 1304 when the received image data is captured with the camera attachment that positions the TRM in a known location in the camera's field of view.

Figure 14:
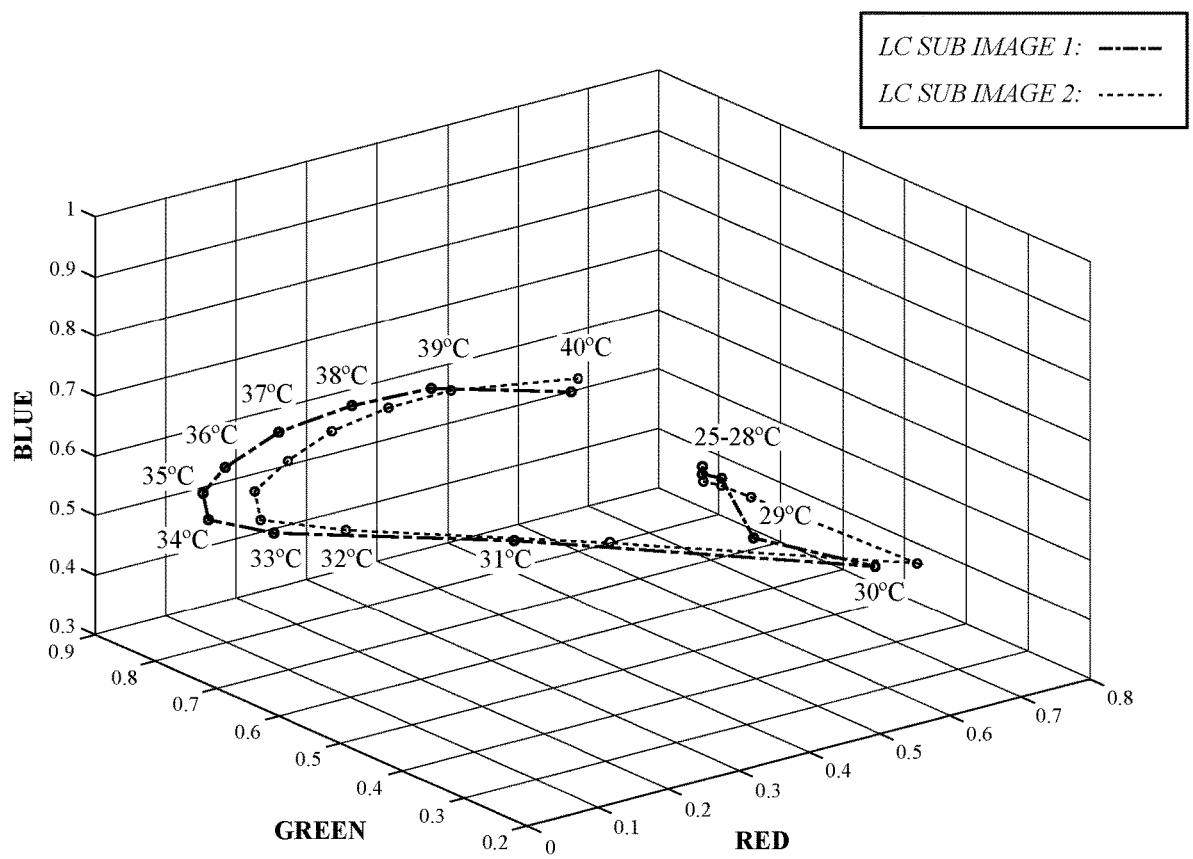
FIG. 14 illustrates an exemplary plot associating RGB values with temperature generated from the set of images illustrated in FIG. 13.

Isolated images 1312, 1314 of the TRM strips are illustrated at the bottom of FIG. 13. In some embodiments, the isolated regions 1308, 1310 include only a portion of the TRM, but in other embodiments, the isolated regions 1308, 1310 include all of the TRM strips. FIG. 14 illustrates an exemplary plot associating RGB values with temperatures generated from the set of images illustrated in FIG. 13. The blue line associates RGB values from the isolated regions 1312 with temperature and the green line associates the RGB values from the isolated regions 1314 with temperature. As can be seen, the Red-Green projection may contain the most temperature information.

Figure 15:
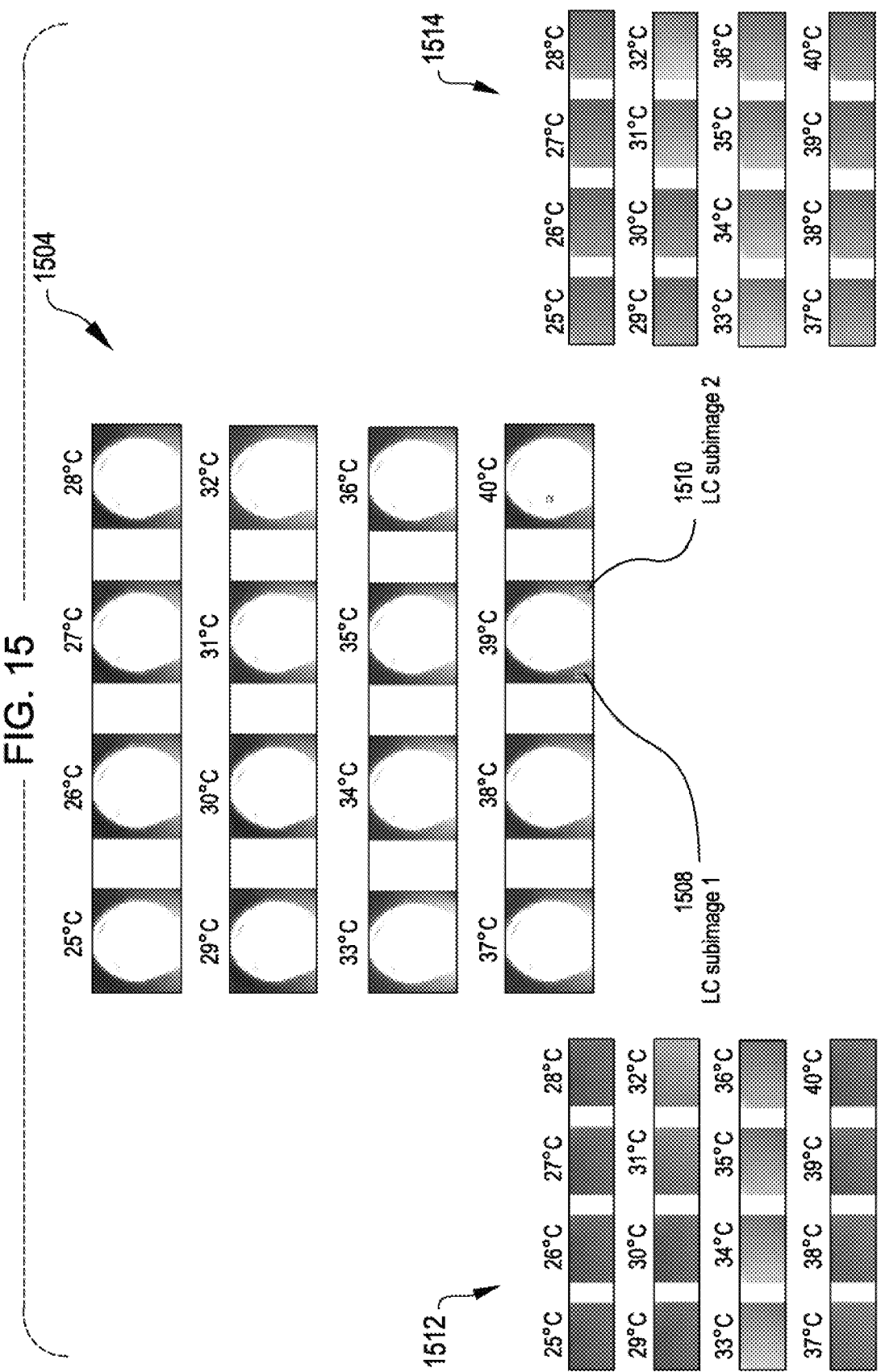
FIG. 15 shows another set of images captured with a camera with a contact assembly similar to that illustrated in FIG. 9.

FIG. 15 illustrates another set of images captured with a camera with a contact member similar to that illustrated in FIG. 9. In the experimental setup, the contact member comprised a metal cap with a white reflector in the image field. Additionally, the contact member comprised a single strip of TRM. FIG. 15 illustrates a plurality of images 1504 of the TRM of the contact member captured by a camera at different temperatures of the TRM strip ranging from 25° C. in the top left image and incrementally increasing by 1° C. to 40° C. in the bottom right image. The temperature of the TRM strip was controlled by a thermoelectric cooler. As can be seen in the captured images 1504, only a portion of the TRM strip is captured in the image data.

Additionally, image data associated with the TRM strip was isolated from the received image data 1504 during image processing for temperature measurement. For example, image 1506 of the plurality of images 1504 in FIG. 13 illustrates exemplary isolated regions 1508, 1510, each associated with the single strip of TRM, where image data associated with the TRM strip was isolated from the image data 1504. Accordingly, in some embodiments, multiple isolated regions (e.g., two, three, four, or more) can be associated with a single TRM strip. This may provide more accurate temperature measurements. The regions 1508, 1510 can be user specified before and/or during image processing. Alternatively, the isolated regions 1508, 1510 can be predetermined locations in the received image data 1504 when the received image data is captured with the camera attachment that positions the TRM in a known location in the camera's field of view. The isolated images 1512, 1514 of the TRM strip are illustrated at the bottom of FIG. 15.

Figure 16:
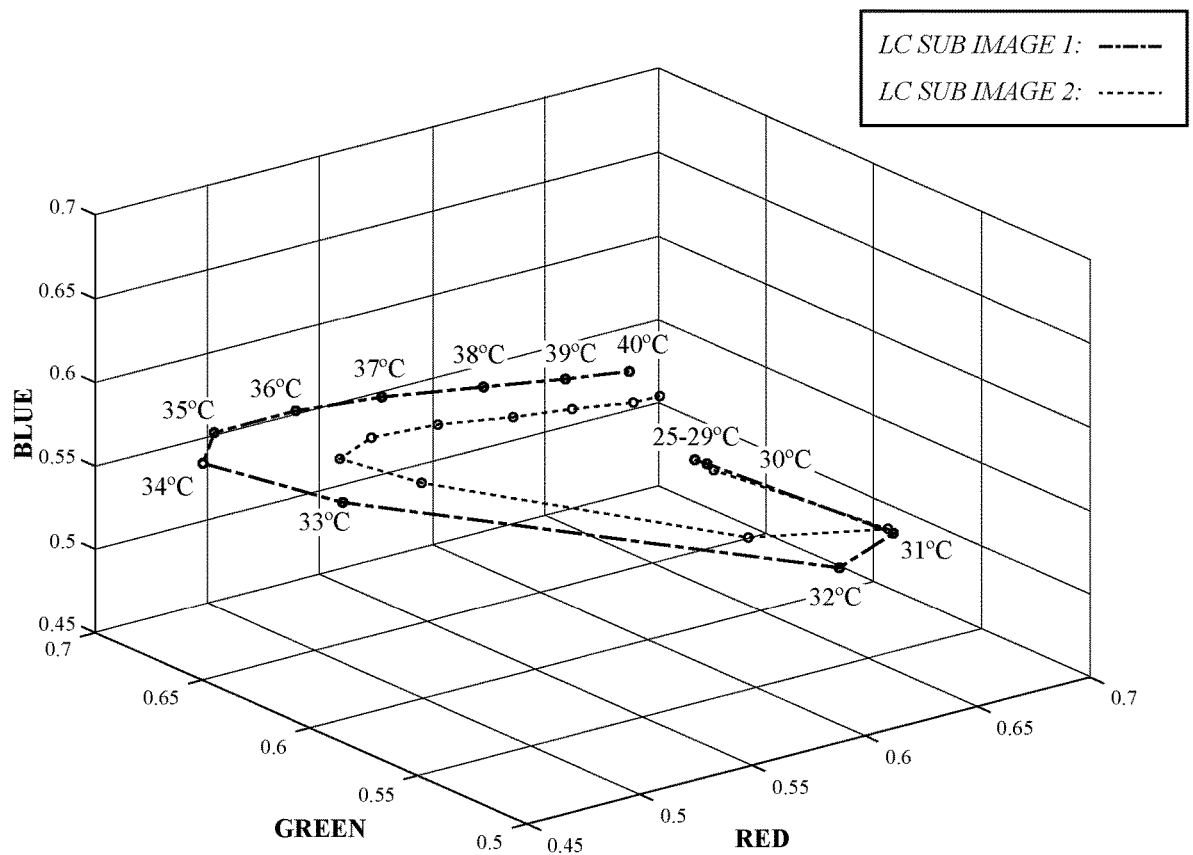
FIG. 16 illustrates an exemplary plot associating RGB values with temperature generated from the set of images illustrated in FIG. 15.

FIG. 16 illustrates an exemplary plot associating RGB values with temperature generated from the set of images illustrated in FIG. 15. The blue line associates RGB values from the isolated regions 1512 with temperature and the green line associates the RGB values from the isolated regions 1514 with temperature. From the images of FIG. 15 and their corresponding plots in FIG. 16, white haze may reduce the span of color change, similar to the experiment illustrated in FIG. 11 and FIG. 13. Again, the Red-Green projection may contain the most temperature information.

Figure 17:
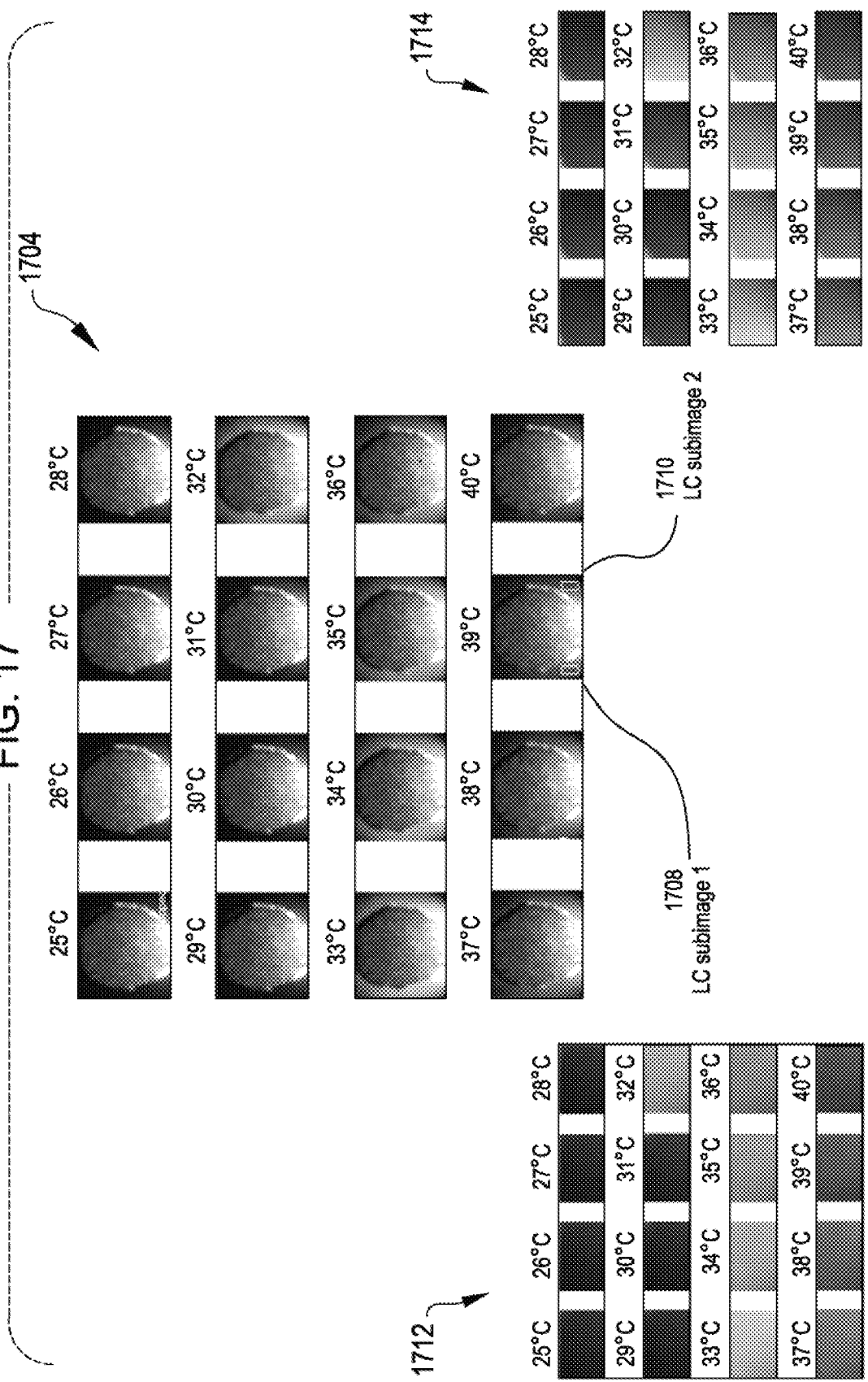
FIG. 17 shows another set of images captured with a camera with a contact assembly similar to that illustrated in FIG. 9.

FIG. 17 illustrates another set of images captured with a camera with a contact member similar to that illustrated in FIG. 9. In the experimental setup, the contact member comprised a metal cap with a black reflector in the image field. Additionally, the contact member comprised a single strip of temperature sensitive material, similar to the contact member used for the experiment shown in FIG. 15. FIG. 17 illustrates a plurality of images 1704 of the TRM of the contact member captured by a camera at different temperatures ranging from 25° C. in the top left image and incrementally increasing by 1° C. to 40° C. in the bottom right image. The temperature of the liquid crystal film was controlled by a thermoelectric cooler. As can be seen in the captured images 1704, only a portion of each of the TRM strips is captured in the image data.

Additionally, image data associated with the TRM strip is isolated from the received image data 1704 during image processing for temperature measurement. For example, the image 1706 of the plurality of images 1704 in FIG. 17 illustrates exemplary isolated regions 1708, 1710, each associated with the single strip of TRM, where image data associated with the TRM strip was isolated from the image data 1704. Accordingly, in some embodiments, multiple isolated regions (e.g., two, three, four, or more) can be associated with a single TRM strip. This may provide more accurate temperature measurements. The regions 1708, 1710 can be user specified before and/or during image processing. Alternatively, the isolated regions 1708, 1710 can be predetermined locations in the received image data 1704 when the received image data is captured with the camera attachment that positions the TRM strip in a known location in the camera's field of view. The isolated images 1712, 1714 of the TRM strip are illustrated at the bottom of FIG. 17.

Figure 18:
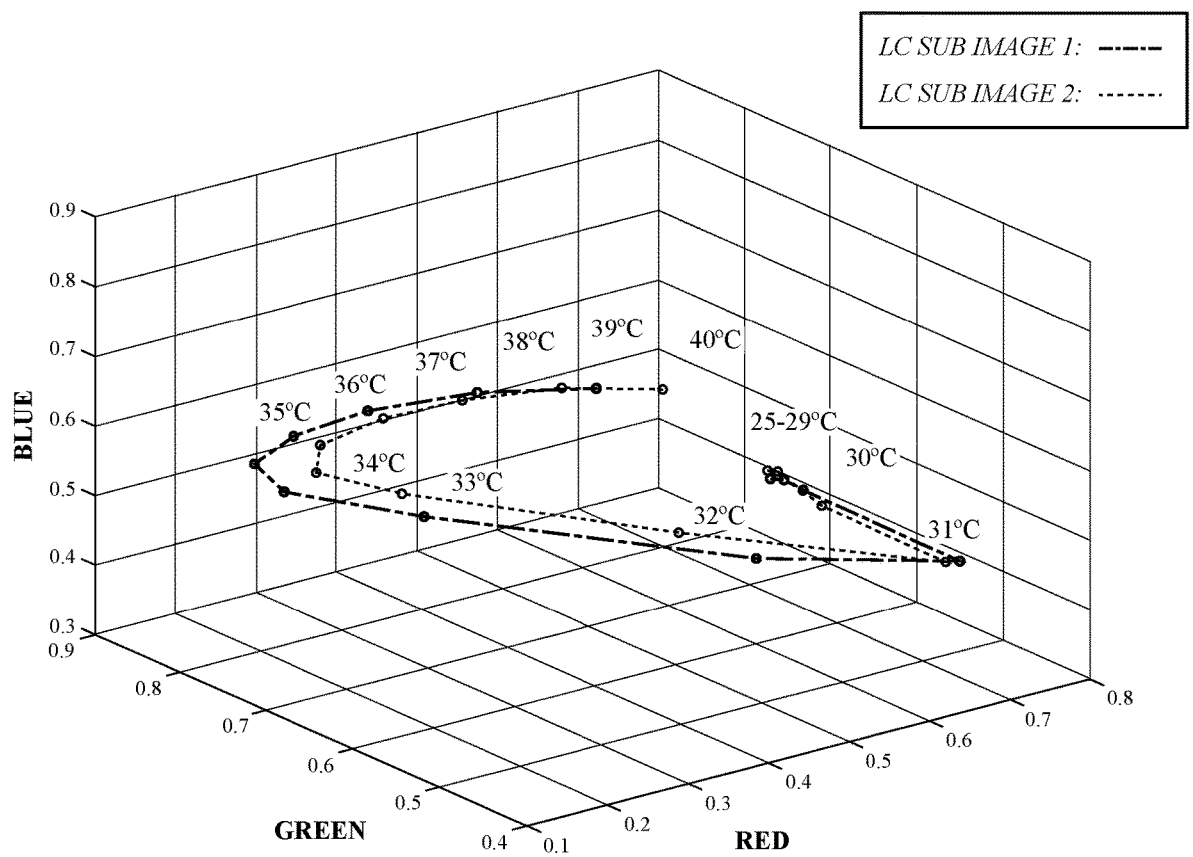
FIG. 18 illustrates an exemplary plot associating RGB values with temperature generated from the set of images illustrated in FIG. 17.

FIG. 18 illustrates an exemplary plot associating RGB values with temperature generated from the set of images illustrated in FIG. 17. The blue line associates RGB values from the isolated regions 1712 with temperature and the green line associates the RGB values from the isolated regions 1714 with temperature.

Figure 19:
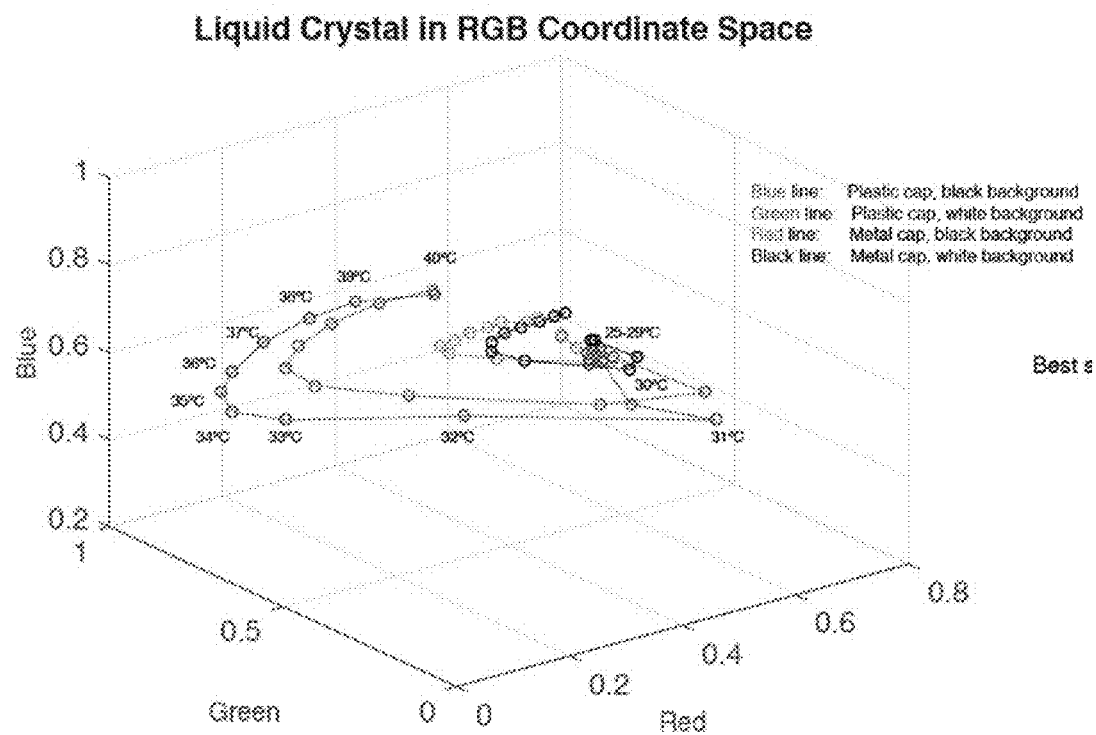
FIG. 19 illustrates a composite of the plots of FIG. 12, FIG. 14, FIG. 16, and FIG. 18.

FIG. 19 illustrates a composite of the plots of FIG. 12, FIG. 14, FIG. 16, and FIG. 18 of the best subimage from each configuration of the contact member. The blue line is associated with the plastic contact member with the black background. The green line is associated with the plastic contact member with the white background. The red line is associated with the metal contact member with the black background. The black line is associated with the metal contact member with the white background. From the plots, it can be seen that non-uniform illumination and reflections from the surface may significantly affect RGB mapping.

Figure 20:
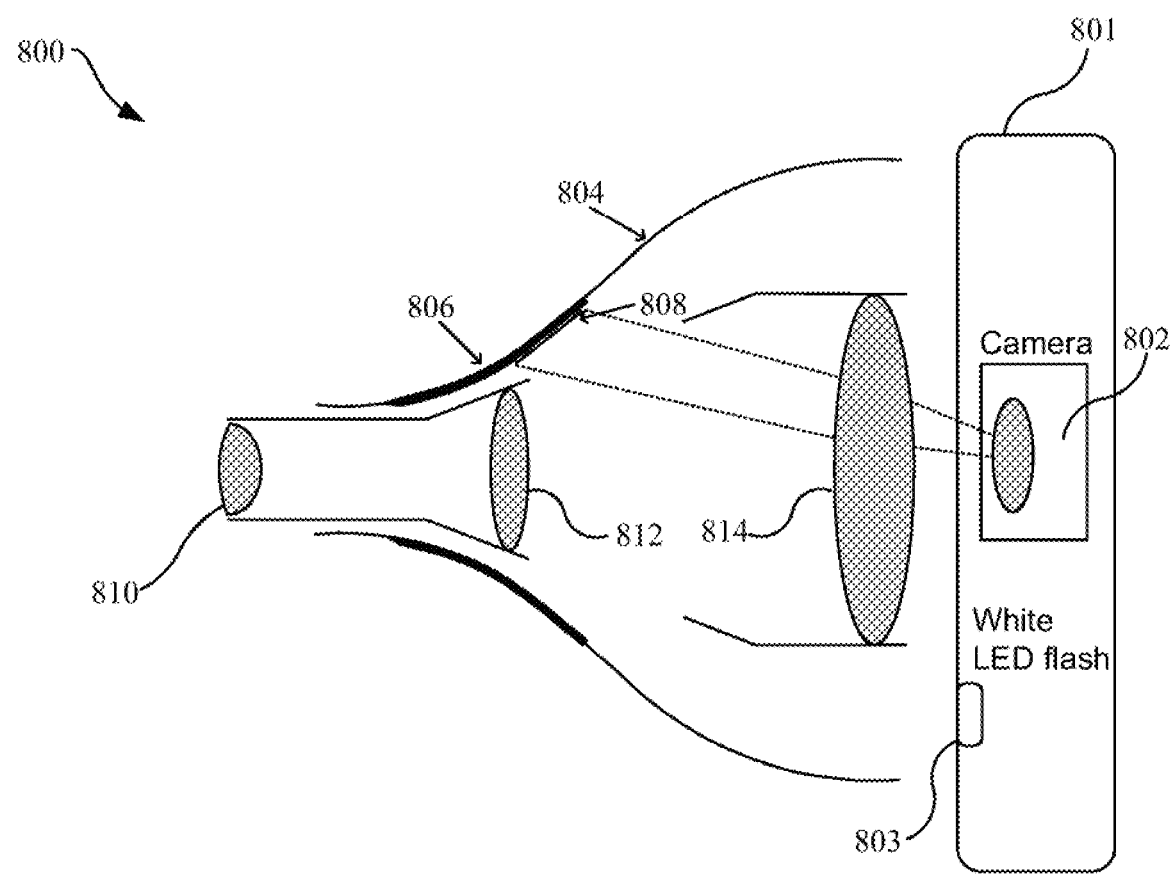
FIG. 20 illustrates another exemplary camera attachment for temperature measurement according to some embodiments.

FIG. 20 illustrates another camera attachment 800 for temperature measurement according to some embodiments. Furthermore, camera attachment 800 can also be used to provide otoscope functionality to an attached camera. In the illustrated embodiment, camera attachment 800 is configured to be attached to a smartphone 801 to cooperate with a camera 802 and the light source 803 of the smartphone 801.

The attachment 800 includes an otoscope cone 804 configured to be inserted distally into an ear of a patient. The cone 804 has a proximal base portion, a distal tip portion, and a neck region disposed between the proximal base portion and the distal tip. The proximal base portion is configured to couple with the distal face of the smartphone 801 and optically couple the attachment 800 with the light source 803 of the smartphone 801. The attachment 800 tapers down from the proximal base portion toward the distal tip portion, which is configured to be inserted into the ear of the patient. The neck region can be configured to contact a surface of the ear to limit insertion depth of the cone 804 into the ear to prevent inadvertent damage to the ear during use. Additionally, the neck region can comprise a thermally conductive material 806 with a distal surface for contacting the ear. A proximal surface of the thermally conductive material 806 can be coupled with a TRM 808.

Cone 804 can house a plurality of lenses 810, 812, 814 for imaging the inside of the ear and can align the lens axes with the camera 802 of the smartphone 801. In the illustrated embodiment, the cone 804 houses lenses 810, 812, and 814. Lens 810 can be at the distal tip of the cone 804. Lens 810 can be at the neck region of cone 804. Lens 814 can be at the proximal base portion of cone 804. The lens 814 can help camera 802 of the smartphone 801 image at least a portion of the TRM 808.

In use, the attachment 800 can be attached to smartphone 801 and inserted into the ear of a patient. During insertion, the neck region can contact the skin of the patient to limit insertion depth. Once inserted, the inside of the ear can be imaged by the camera 802. Additionally, the thermally conductive material 806 will equilibrate with the patient's temperature and the TRM 808 will change color in response. During imaging of the inside of the ear, the camera 802 also capture images of the TRM 808. The cone 804 can also include a light pipe (e.g., similar to light pipe 606) or other optical components for guiding light from the light source 803 toward the inside of the ear and/or toward the TRM 808 to facilitate viewing and imagining of the inside of the ear and the TRM 808. The smartphone 801 can then measure a temperature of the TRM 808 using the methods described herein and can output the temperature to the physician/user. In some embodiments, the smartphone 801 can image the ear simultaneously with the temperature measurement. The processing can isolate the image of the TRM from the ear image and can separately process the isolated imaged of the TRM to measure temperature. Thereafter, the smartphone can output the image of the ear in combination with the temperature measurement.

The illustrated attachment 800 is described with specificity, but it should be understood that other modifications are possible. For example, attachment 800 can include one or more mirrors for imaging the TRM 808 with camera 802. Additionally, while illustrated with three lenses, 810, 812, and 814, other embodiments can utilized fewer or more lenses. Similarly, while illustrated with a single strip of TRM 808, other embodiments can include multiple strips (e.g., for different temperature ranges or for spaced apart locations for better temperature measurements)

While the camera attachments 600, 800 provides dual functionality, i.e., temperature measurement and optical instrument, it should be understood that the camera attachment may be specific for temperature measurement alone. For example, in some embodiments, an attachment can be provided that includes a TRM and that does not include separate lens or an aperture to allow the camera to image anything other than the TRM. The attachment may nevertheless provide temperature measurements by relying solely on the smartphone's native imaging capabilities in combination with image processing techniques to derive temperature from the image data associated with the TRM.

One or more computing devices can be adapted to provide desired functionality by accessing software instructions rendered in a computer-readable form. When software is used, any suitable programming, scripting, or other type of language or combinations of languages can be used to implement the teachings contained herein. However, software need not be used exclusively, or at all. For example, some embodiments of the methods and systems set forth herein can also be implemented by hard-wired logic or other circuitry, including but not limited to application-specific circuits. Combinations of computer-executed software and hard-wired logic or other circuitry may be suitable as well.

Embodiments of the methods disclosed herein can be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMs, DVD-ROMs, variants thereof, etc.), flash, RAM, ROM, and other memory devices, and the like.

The subject matter of embodiments of the present disclosure is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

It will be appreciated that personal information data may be utilized in a number of ways to provide benefits to a user of a device. For example, personal information such as health or biometric data may be utilized for convenient authentication and/or access to the device without the need of a user having to enter a password. Still further, collection of user health or biometric data (e.g., temperature measurements) may be used to provide feedback about the user's health and/or fitness levels. It will further be appreciated that entities responsible for collecting, analyzing, storing, transferring, disclosing, and/or otherwise utilizing personal information data are in compliance with established privacy and security policies and/or practices that meet or exceed industry and/or government standards, such as data encryption. For example, personal information data should be collected only after receiving user informed consent and for legitimate and reasonable uses of the entity and not shared or sold outside those legitimate and reasonable uses. Still further, such entities would take the necessary measures for safeguarding and securing access to collected personal information data and for ensuring that those with access to personal information data adhere to established privacy and security policies and/or practices. In addition, such entities may be audited by a third party to certify adherence to established privacy and security policies and/or practices. It is also contemplated that a user may selectively prevent or block the use of or access to personal information data. Hardware and/or software elements or features may be configured to block use or access. For instance, a user may select to remove, disable, or restrict access to certain health related applications that collect personal information, such as health or fitness data. Alternatively, a user may optionally bypass biometric authentication methods by providing other secure information such as passwords, personal identification numbers, touch gestures, or other authentication methods known to those skilled in the art.

Different arrangements of the components depicted in the drawings or described above, as well as components and steps not shown or described are possible. Similarly, some features and sub-combinations are useful and may be employed without reference to other features and sub-combinations. Embodiments of the disclosure have been described for illustrative and not restrictive purposes, and alternative embodiments will become apparent to readers of this patent. Accordingly, the present disclosure is not limited to the embodiments described above or depicted in the drawings, and various embodiments and modifications may be made without departing from the scope of the claims below.

What is claimed is:

1. An electronic device, comprising:
   a camera;
   a frame disposed adjacent the camera and having an aperture disposed along an optical axis of the camera;
   a temperature reactive material attached to the frame and positioned at a periphery of a field of view of the camera; and
   a processor configured to operate the camera and capture a composite image including,
      a central image of an object positioned exterior to the frame; and
      a peripheral image of the temperature reactive material.

2. The electronic device of claim 1, wherein the electronic device comprises further comprising a smartphone housing in which the camera is mounted.

3. The electronic device of claim 2, wherein the frame is detachable from the smartphone housing.

4. The electronic device of claim 1, wherein the temperature reactive material is positioned within the field of view of the camera.

5. The electronic device of claim 1, wherein:
   the temperature reactive material is positioned outside the field of view of the camera; and
   the electronic device further comprises a reflector configured disposed positioned to reflect an image of the temperature reflective material into the field of view of the camera.

6. The electronic device of claim 1, wherein the temperature reactive material is in thermal contact with the frame.

7. The electronic device of claim 1, wherein:
   the processor is configured to,
      in a temperature analysis mode, determine a temperature using the peripheral image; and
      in a camera mode, display the central image to a user of the electronic device.

8. The electronic device of claim 7, wherein:
   the processor is configured to,
      in the temperature analysis mode, display the central image and the temperature to the user.

9. The electronic device of claim 1, wherein the temperature reactive material comprises a thermo-chromic liquid crystal film.

10. An electronic device, comprising:
    a camera;
    a temperature reactive material positioned at a periphery of a field of view of the camera; and a processor configured to operate the camera and capture a composite image including,
a central image of an object positioned exterior to the electronic device; and
a peripheral image of the temperature reactive material.

11. The electronic device of claim 10, further comprising:
a flash unit associated with the camera; and
a light guide configured to direct at least a portion of light emitted by the flash unit toward the temperature reactive material.

12. The electronic device of claim 10, further comprising a lens positioned between the camera and the temperature reactive material.

13. The electronic device of claim 10, wherein the camera is a color image-based camera.

14. An electronic device, comprising:
a camera;
a frame having a proximal portion, a distal portion, a neck region disposed between the proximal portion and the distal portion, the proximal portion closest to the camera, and the distal portion defining an aperture through which the camera acquires images of objects positioned exterior to the electronic device; and
a temperature reactive material positioned adjacent the neck region of the frame; wherein,
the camera is configured to capture a composite image of the objects positioned exterior to the electronic device and the temperature reactive material positioned adjacent the neck region of the frame.

15. The electronic device of claim 14, wherein the temperature reactive material is positioned on the neck region and within the frame.

16. The electronic device of claim 14, further comprising a mirror attached to the frame, the mirror directing an image of the temperature reactive material toward the camera.

17. The electronic device of claim 14, further comprising a thermally conductive material connecting the temperature reactive material to an exterior surface of the electronic device.

18. The electronic device of claim 17, wherein the thermally conductive material comprises the neck region of the frame.

19. The electronic device of claim 14, wherein the frame defines an otoscope cone.

* * * * *